(12) United States Patent
Weksler et al.

(10) Patent No.: US 9,709,708 B2
(45) Date of Patent: Jul. 18, 2017

(54) ADJUSTABLE DISPLAY OPTICS

(71) Applicant: Lenovo (Singapore) Pte. Ltd., Singapore (SG)

(72) Inventors: Arnold S. Weksler, Raleigh, NC (US); John Carl Mese, Cary, NC (US); Rod D. Waltermann, Rougemont, NC (US); Russell Speight VanBlon, Raleigh, NC (US); Nathan J. Peterson, Durham, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 242 days.

(21) Appl. No.: 14/100,593

(22) Filed: Dec. 9, 2013

(65) Prior Publication Data
US 2015/0160380 A1    Jun. 11, 2015

(51) Int. Cl.
| G02B 3/12  | (2006.01) |
| G02B 3/14  | (2006.01) |
| G02B 27/02 | (2006.01) |
| G02B 27/00 | (2006.01) |
| A61B 3/00  | (2006.01) |
| A61B 3/032 | (2006.01) |
| G02B 3/08  | (2006.01) |

(52) U.S. Cl.
CPC .............. *G02B 3/14* (2013.01); *A61B 3/0041* (2013.01); *A61B 3/032* (2013.01); *G02B 27/0068* (2013.01); *G02B 27/027* (2013.01); *G02B 3/08* (2013.01)

(58) Field of Classification Search
USPC ................................................ 359/666, 665
See application file for complete search history.

(56) References Cited

U.S. PATENT DOCUMENTS

| 2,510,344 A | 6/1950  | Law              |
| 2,567,654 A | 9/1951  | Siezen           |
| 3,418,426 A | 12/1968 | Schlegel et al.  |
| 3,628,854 A | 12/1971 | Jampolsky        |
| 4,082,433 A | 4/1978  | Appeldorn et al. |
| 4,190,330 A | 2/1980  | Berreman         |
| 4,577,928 A | 3/1986  | Brown            |
| 5,579,037 A | 11/1996 | Tahara et al.    |
| 5,583,702 A | 12/1996 | Cintra           |

(Continued)

FOREIGN PATENT DOCUMENTS

| DE | 10310794 | 9/2004  |
| DE | 69937592 | 10/2008 |

(Continued)

OTHER PUBLICATIONS

Russell Speight VanBlon. Neal Robert Caliendo Jr.: "Automatic Magnification and Selection Confirmation" file history of related U.S. Appl. No. 14/322,119, filed Jul. 2, 2014.

(Continued)

*Primary Examiner* — Jack Dinh
(74) *Attorney, Agent, or Firm* — Brian J. Pangrle

(57) ABSTRACT

A system can include a display configured to emit light rays; an adjustable-prescription optics overlay; and circuitry to adjust the adjustable-prescription optics overlay to a selected prescription to alter a focus of light rays emitted by at least a portion of the display. Various other apparatuses, systems, methods, etc., are also disclosed.

16 Claims, 12 Drawing Sheets

(56) References Cited

U.S. PATENT DOCUMENTS

| | | | |
|---|---|---|---|
| 6,046,847 | A | 4/2000 | Takahashi |
| 6,417,894 | B1 * | 7/2002 | Goff ....................... G02B 7/023 348/832 |
| 2004/0160419 | A1 | 8/2004 | Padgitt |
| 2009/0065578 | A1 | 3/2009 | Peterson et al. |
| 2009/0204410 | A1 | 8/2009 | Mozer et al. |
| 2009/0259349 | A1 | 10/2009 | Golenski |
| 2009/0315740 | A1 | 12/2009 | Hildreth et al. |
| 2010/0079508 | A1 | 4/2010 | Hodge et al. |
| 2010/0171720 | A1 | 7/2010 | Craig et al. |
| 2010/0211918 | A1 | 8/2010 | Liang et al. |
| 2011/0065451 | A1 | 3/2011 | Danado et al. |
| 2012/0149309 | A1 | 6/2012 | Hubner et al. |
| 2012/0220311 | A1 | 8/2012 | Rodriguez et al. |
| 2012/0268268 | A1 | 10/2012 | Bargero |
| 2013/0021459 | A1 | 1/2013 | Vasilieff et al. |
| 2013/0044042 | A1 | 2/2013 | Olsson et al. |
| 2013/0170755 | A1 | 7/2013 | Dalton et al. |
| 2013/0246663 | A1 | 9/2013 | Raveendran et al. |
| 2013/0307771 | A1 | 11/2013 | Parker et al. |
| 2014/0317524 | A1 | 10/2014 | VanBlon et al. |

FOREIGN PATENT DOCUMENTS

| | | |
|---|---|---|
| EP | 0880090 | 11/1998 |
| WO | 2004051392 | 6/2004 |

OTHER PUBLICATIONS

Russell Speight VanBlon, Neal Robert Caliendo Jr.: "Magnification Based on Eye Input" file history of related U.S. Appl. No. 14/546,962, filed Nov. 18, 2014.

Russell Speight VanBlon, Suzanne Marion Beaumont. Rod David Waltermann. "Detecting Pause in Audible Input to Device" file history of related U.S. Appl. No. 14/095,369, filed Dec. 3, 2013.

Suzanne Marion Beaumont. Russell Speight VanBlon, Rod D. Waltermann, Devices and Methods to Receive Input at a First Device and Present Output in Response on a Second Device Different from the First Device file history of related U.S. Appl. No. 14/095,093, filed Dec. 3, 2013.

Jonathan Gaither Knox, Rod D. Waltermann. Liang Chen, Mark Evan Cohen, "Initiating Personal Assistant Application Based on Eye Tracking and Gestures" file history of related U.S. Appl. No. 14/095,235, filed Dec. 3, 2013.

Nathan J. Peterson, John Carl Mese, Russell Speight VanBlon. Arnold S. Weksler, Rod D. Waltermann, Xin Fend, Howard J. Locker. "Systems and Methods to Present Information on Device Based on Eye Tracking" file history of related U.S. Appl. No. 14/132,663, filed Dec. 18, 2013.

Russell Speight VanBlon. Rod David Waltermann, John Carl Mese. Arnold S. Weksler. Nathan J. Peterson, "Detecting Noise or Object Interruption in Audio Video Viewing and Altering Presentation Based Thereon" fie history of related U.S. Appl. No. 14/158,990, filed Jan. 20, 2014.

Russell Speight VanBlon, Axel Ramirez Flores, Jennifer Greenwood Zawacki, Alan Ladd Painter, "Skin Mounted Input Device" fife history of related U.S. Appl. No. 14/1162,115, filed Jan. 23, 2014.

Steven Richard Perrin, Jianbang Zhang, John Weldon. Scott Edwards Kelso, "Initiating Application and Performing Function Based on Input" file history of related U.S. Appl. No. 14/557,628, filed Dec. 2, 2014.

Rod David Waltermann, John Carl Mese, Nathan J. Peterson, Arnold S. Weksler, Russell Speight VanBlon, Movement of Displayed Element from One Display to Another file history of related U.S. Appl. No. 14/1550,107, filed Nov. 21, 2014.

Amy Leigh Rose: Nathan J. Peterson, John Scott Crowe, Bryan Loyd Young, Jennifer Lee-Baron, "Presentation of Data on an at Least Partially Transparent Display Based an User Focus" file history of related U.S. Appl. No. 14/548,938, filed Nov. 20, 2014.

Wikipedia. "Electromyography". definition: http://en.wikipedia.org/wiki/Electromyogrpahy, printed from website Jan. 27, 2015.

Isource: "Raise to Speak Makes Siri Wonderfully Useful (Once You Know How to Use It)", http:///isourcecom/10/01/raise-to-speak-makes-siri-wonderfurly-useful-once-you-know-how-to-use-itl Web printout Nov. 15, 2013.

Wikipedia. "Microphone array"; definition, http://en.wikipe-dia.org/wiki/Microphone_array, printed from website Jan. 22, 2015.

Wikipedia, "Microphone", definition; httbliertwilipedia.org/wkik/microphone. printed from website Jan. 22, 2015.

Thalmiclabs, "Myo Gesture Control Armband" http://www.thalmic_cornien/myo, printed from website Jan. 27, 2015.

Thalmiclabs. "Myo-Tech Specs", http://www.thalmic.com/en/nnyoftechspec,s, printed from website Jan. 27, 2015.

Wikipedia, "Beamfoming", definition: http://en.wikipedia.orglwikiiBeamforming, printed from website Jan. 22, 2015.

Wikipedia, "Extended Display Identification Data", Definition; http://en.wikipedia,org/wiki/Extencied_display_Identification_data. printed from website Oct. 10, 2014.

Extron , Digital Connection, Understanding ED]D—Extended Display Identification Data, Fail 2009, www.extron.com.

"Relationship Between Inches: Picas, Points. Pitch, and Twips", Article ID: 76388 http://support2,microsoftoom/KB/76388, Printed Oct. 10, 2014.

Wikipedia, "Polarizer" Definition: http://en.wikipedia.org/wiki/Polari2er. printed from website Jan. 14, 2015.

Wikepedia, "Smart Glass" Definition, http//en.wikipedia.orgiwiki/Smart_glass, printed from website Jan. 14, 2015.

Understanding & Using Directional Microphones, http:Thomv_soundonsound.com/sosisep00/articiesidirection.htm: Published in SOS Sep. 2000.

Superfocus—Keep your world in focus. Retrieved on Jun. 24, 2014 from http://superfocus.com/ (6 pages).

Darren Quick, "PixelOptics to launch 'world's first electronic focusing eyewear'" Jan. 12, 2011, http://www.gizmag.com/pixeloptics-empower-electronic-focusing-glasses/17569/. (6 pages).

"Electronic-lens company PixelOptics is bankrupt", Dec. 12, 2013, http://vvww.insightnews.com.au/_blog/NEVVS_NOWI/post/electronics-lens-company-pixeloptics-is-bankrupt/ (3 pages).

Tactus Technology, "Taking Touch Screen Interfaces Into a New Dimension", 2012 (13 pages).

Davis et al., "Optical Design using Fresnel Lenses", Optik & Photnik, Dec. 2007, No. 4, p. 52 (4 pages).

* cited by examiner

Blurry Image 102
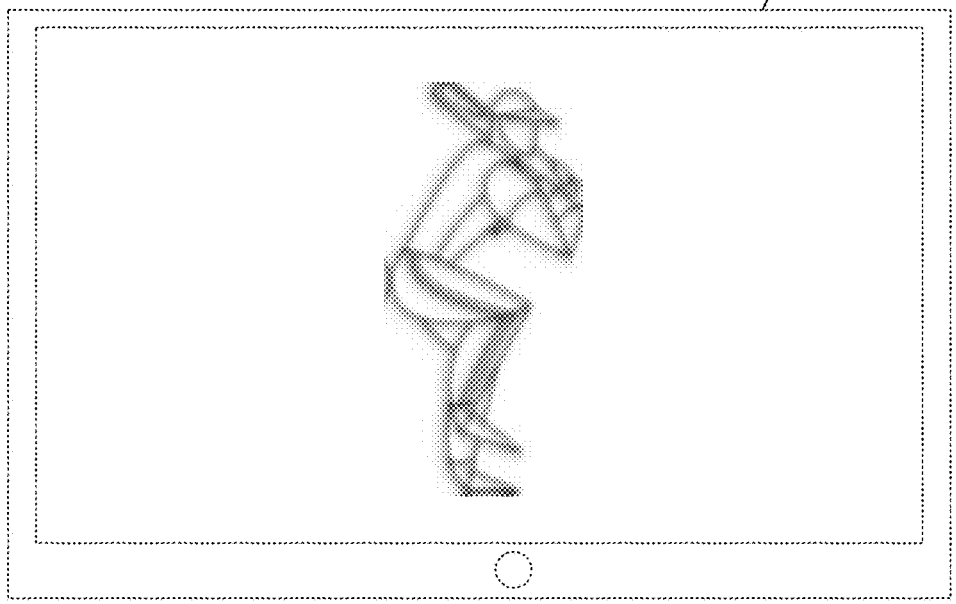
Corrected Image 104
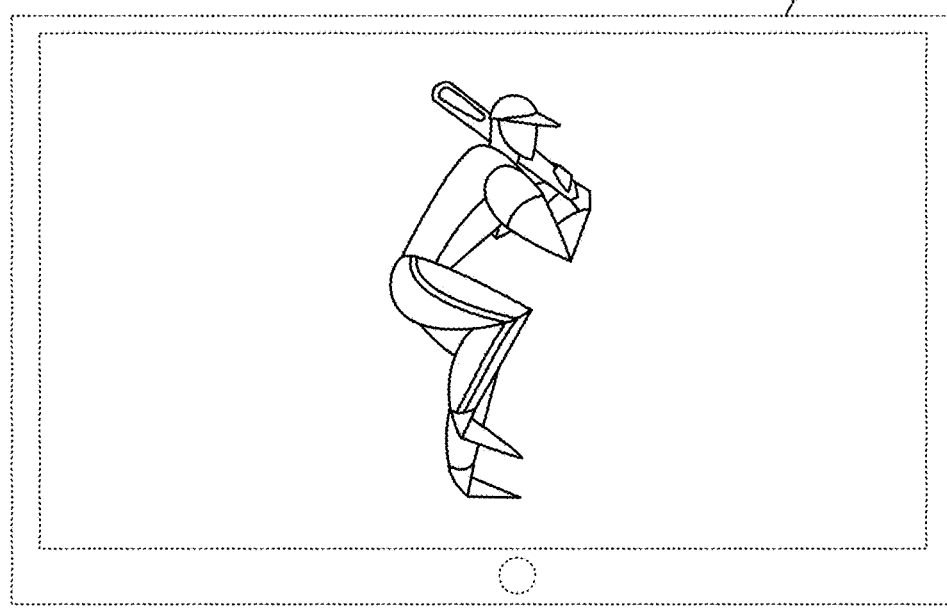
Optical Correction Module 110
FIG. 1

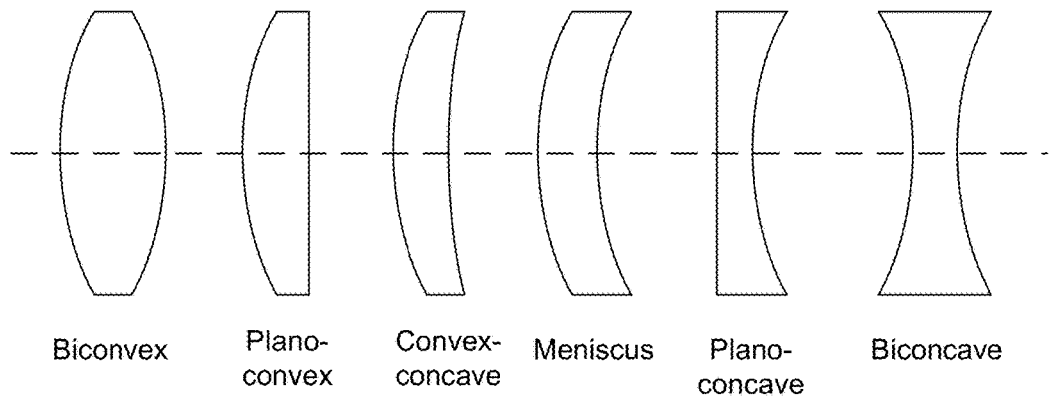
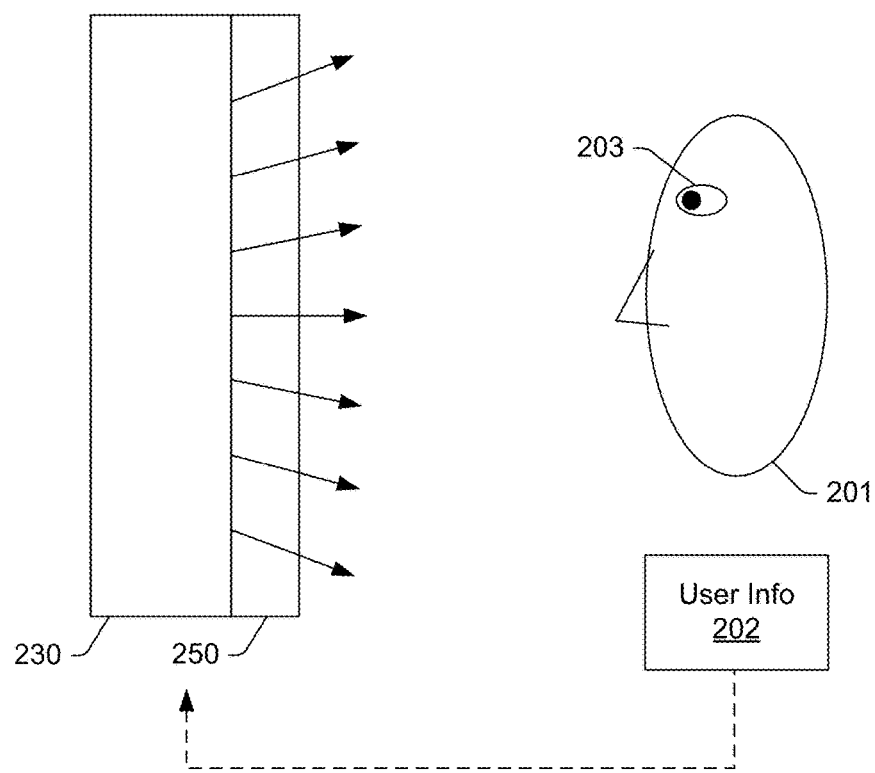
FIG. 2

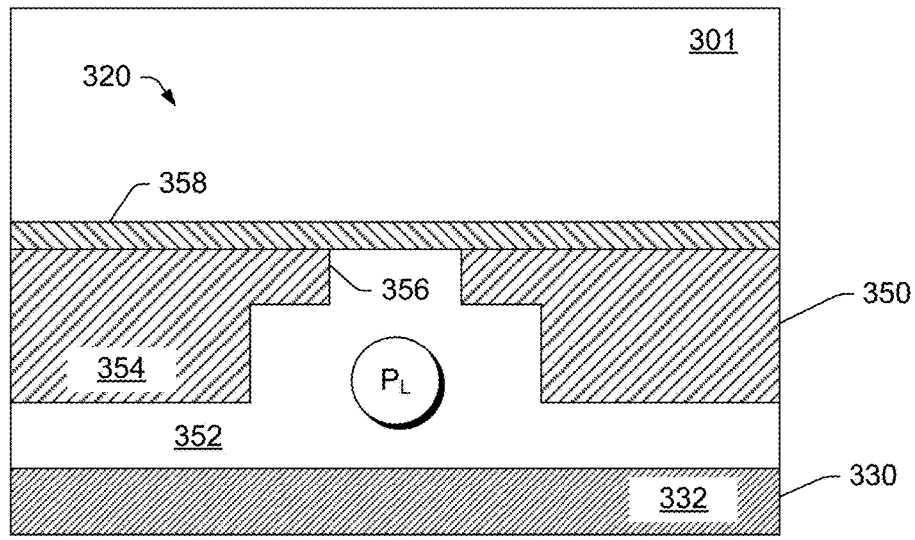
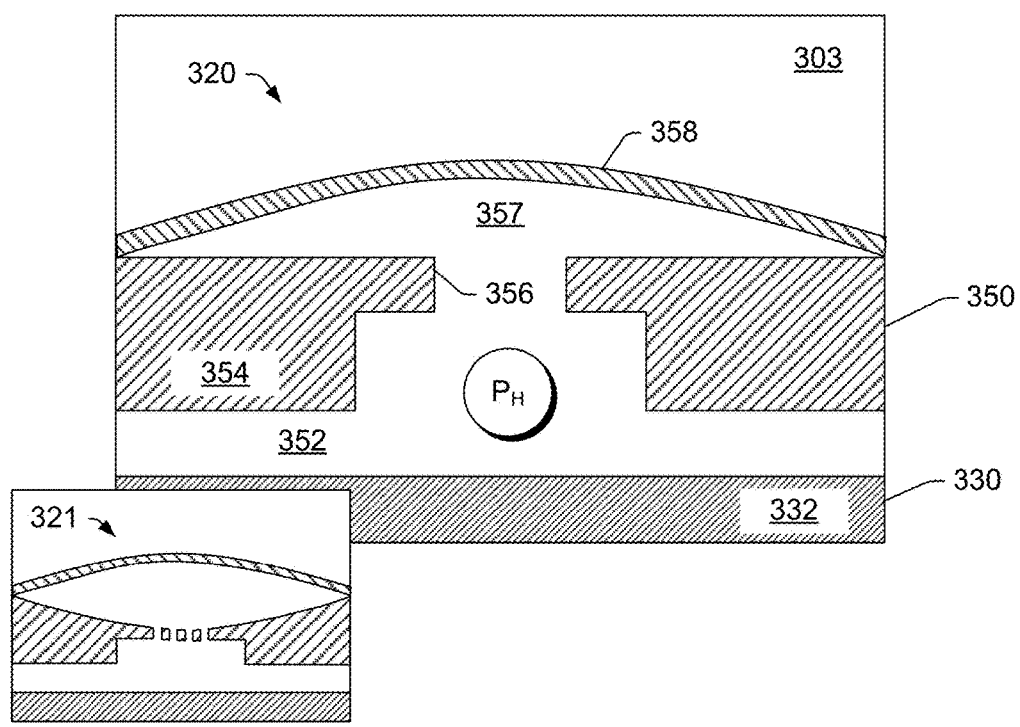
FIG. 3

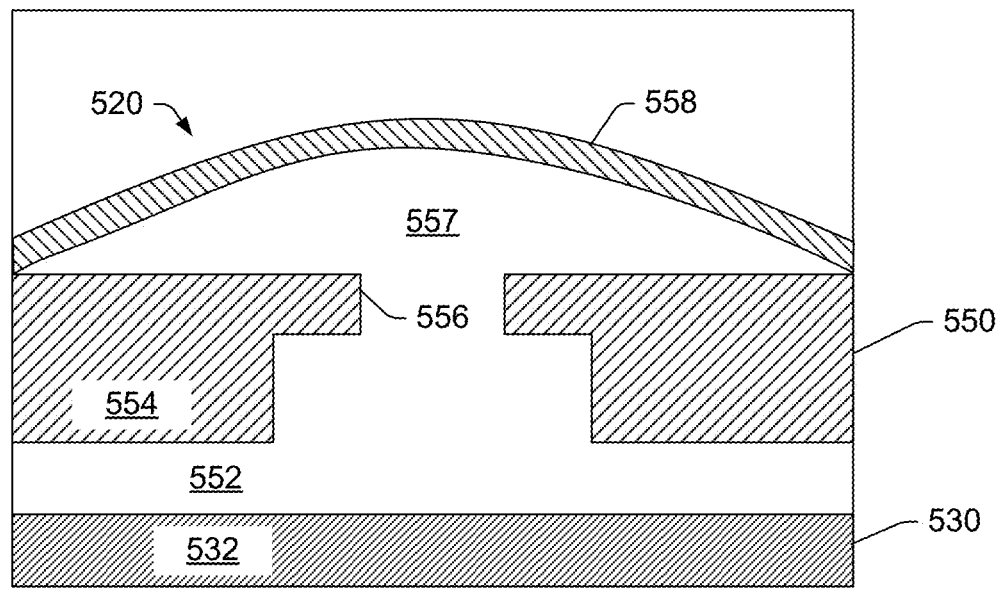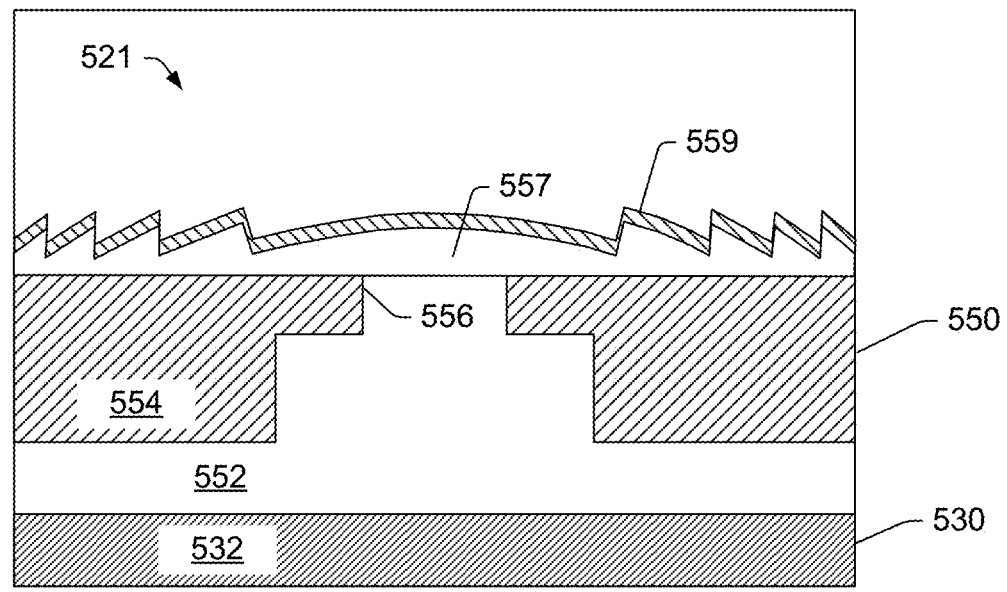
FIG. 5

620                601

"There is a concatenation of events in this best of all possible worlds: for if you had not been kicked out of a magnificent castle for love of Miss Cunegonde: if you had not been put into the Inquisition: if you had not walked over America: if you had not stabbed the Baron: if you had not lost all your sheep from the fine country of El Dorado: you would not be here eating preserved citrons and pistachio-nuts."

"All that is very well," answered Candide, "but let us cultivate our garden."

---

620                603

"There is a concatenation of events in this best of all possible worlds: for if you had not been kicked out of a magnificent castle for love of Miss Cunegonde: if you had not been put into the Inquisition: if you had not walked over America: if you had not stabbed the Baron: if you had not lost all your sheep from the fine country of El Dorado: you would not be here eating preserved citrons and pistachio-nuts."

"All that is very well," answered Candide, "but let us cultivate our garden."

Optical Correction Module 610

"There is a concatenation of events in this best of all possible worlds: for if you had not been kicked out of a magnificent castle for love of Miss Cunegonde: if you had not been put into the Inquisition: if you had not walked over America: if you had not stabbed the Baron: if you had not lost all your sheep from the fine country of El Dorado: you would not be here eating preserved citrons and pistachio-nuts."

"All that is very well," answered Candide, "but let us cultivate our garden."

701

720                                                                                                   750

"There is a concatenation of event{ best of all possible worlds: for if you had not been kicked out of a magnificent castle for love of Miss Cunegonde: if you had not been put into the Inquisition: if you had not walked over America: if you had not stabbed the Baron: if you had not lost all your sheep from the fine country of El Dorado: you would not be here eating preserved citrons and pistachio-nuts."

"All that is very well," answered Candide, "but let us cultivate our garden."

720
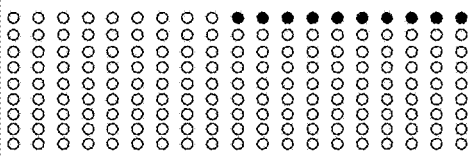
703

703

Optical Correction Module 710

FIG. 7

ADJUSTABLE DISPLAY OPTICS

TECHNICAL FIELD

Subject matter disclosed herein generally relates to optics.

BACKGROUND

Various devices, systems, etc. include a display for display of information (e.g., text, images, graphics, etc.). Various technologies and techniques described herein pertain to display of information, for example, with respect to a viewer.

SUMMARY

A system can include a display configured to emit light rays; an adjustable-prescription optics overlay; and circuitry to adjust the adjustable-prescription optics overlay to a selected prescription to alter a focus of light rays emitted by at least a portion of the display. Various other apparatuses, systems, methods, etc., are also disclosed.

BRIEF DESCRIPTION OF THE DRAWINGS

Features and advantages of the described implementations can be more readily understood by reference to the following description taken in conjunction with examples of the accompanying drawings.

FIG. 1 is a diagram of an example of a blurry image and an example of a corrected image;

FIG. 2 is a diagram of examples of lens types and an example of a system that includes a display and adjustable optics;

FIG. 3 is a diagram of examples of systems;

FIG. 5 is a series of diagrams of examples of systems;

FIG. 6 is a diagram of an example of unmagnified text and an example of magnified text;

FIG. 7 is a diagram of an example of unmagnified text and an example of a portion of the text as magnified text;

DETAILED DESCRIPTION

Figure 4:
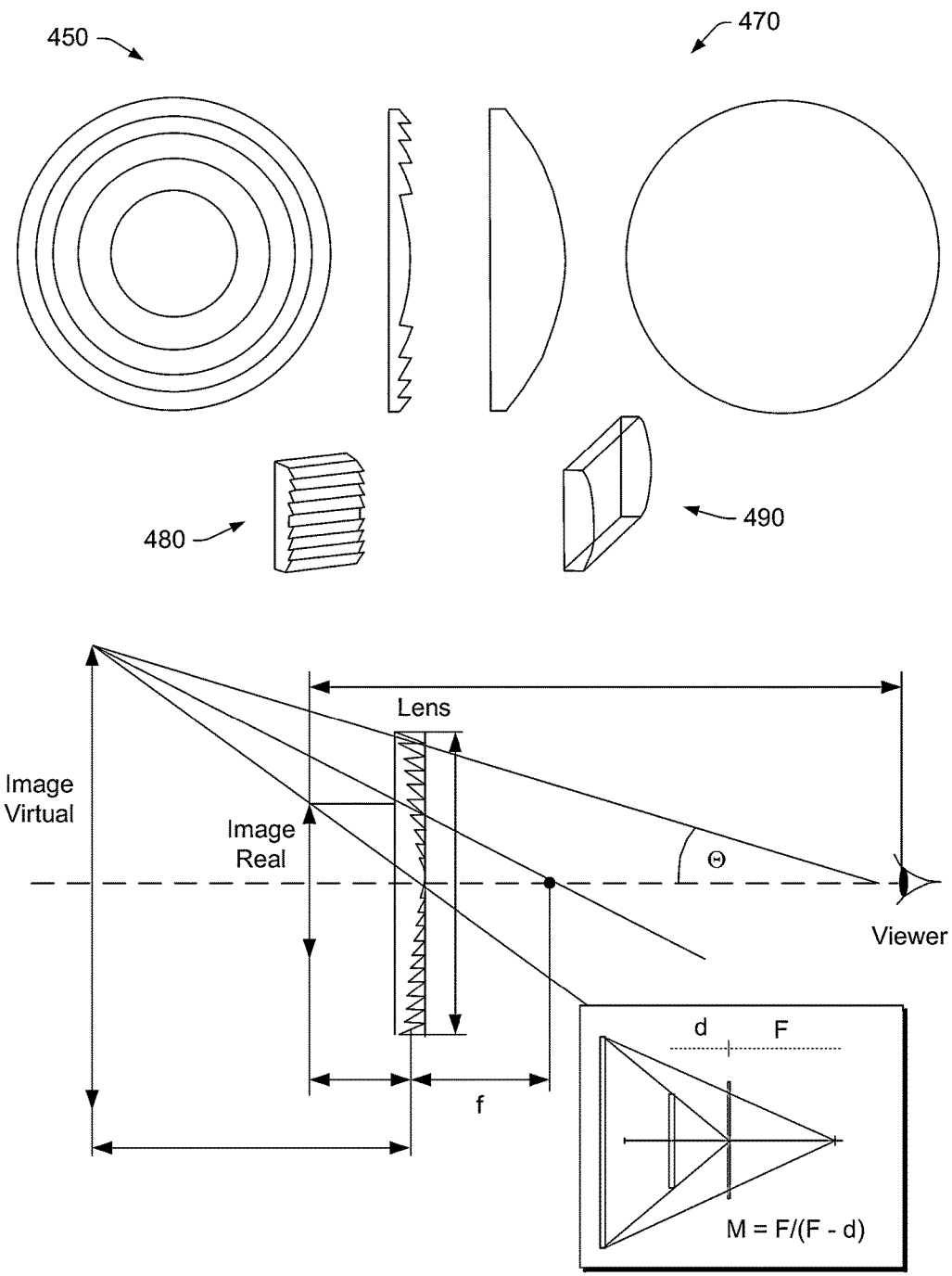
FIG. 4 is a series of diagrams of examples of lenses.

The following description includes the best mode presently contemplated for practicing the described implementations. This description is not to be taken in a limiting sense, but rather is made merely for the purpose of describing general principles of various implementations. The scope of invention should be ascertained with reference to issued claims.

For various reasons, a user may have a less than optimal viewing experience of information rendered to a display. For example, a user may have suboptimal vision, for example, being prescribed reading glasses, glasses for nearsightedness, glasses for farsightedness, etc. (e.g., eyesight correction devices).

Prescription parameters may include power to which a lens should be made to correct blurred vision due to refractive errors, including myopia, hyperopia, astigmatism, presbyopia, etc. As to some examples: DV is an abbreviation for distance vision that specifies the part of the prescription designed primarily to improve far vision; NV is an abbreviation for near vision and may represent a single-vision lens prescription to improve near work, or the reading portion of a bifocal lens (noting that some prescription forms use ADD in place of NV with a single box to indicate the additional refractive power to be added to the spherical of each eye); OD is an abbreviation for oculus dexter (right eye from the patient's point of view); OS is an abbreviation for oculus sinister (left eye from the patient's point of view); OU is an abbreviation for oculi uterque (both eyes); a spherical correction corrects refractive error of the eye with a single convergent or divergent refractive power in all meridians; a cylindrical correction corrects astigmatic refractive error of the eye by adding or subtracting power cylindrically in a meridian specified by the prescribed axis; the axis indicates the angle in degrees of one of two major meridians the prescribed cylindrical power is in (e.g., measured on an imaginary semicircle with a horizontal baseline that starts with zero degrees in the 3 o'clock (e.g., or east) direction, and increases to 180 degrees in a counter-clockwise direction); and diopters are units for spherical and cylindrical lens powers.

As an example, a user may choose to wear or not wear glasses, contact lenses, etc. at certain times or may find that her vision has changed and that a prescription is out-of-date or otherwise suboptimal for viewing displayed information. Further, a user may have a variety of devices with displays where each display is best viewed at a particular distance, for example, where a user's glasses, contact lenses, etc. may be suboptimal over the range of such distances. For example, a user may have a so-called smart watch, a tablet, a laptop and a desktop computer (e.g., in an all-in-one configuration or with a separate display). In such an example, the user's glasses, even if bifocal or progressive, may not adequately cover the best ranges for viewing displays associated with these devices.

As an example, a user's viewing experience may be improved through use of optics. For example, a system may include a display for emitting light rays and adjustable optics. In such an example, the adjustable optics may alter the light rays emitted by the display in a manner that enhances viewing experience for a user or users.

As an example, adjustable optics may be set to a prescription (e.g., for one eye, for two eyes, a compromise value or values, etc.) and be selectively enabled and disabled to correct displayed information according to the prescription. As an example, adjustable optics may be adjustable to one or more prescriptions, for example, based on user information. For example, where a device with a display is used by more than one user, the device may provide for input of information to determine which prescription to use for adjusting optics for the display. As an example, Joe may have a prescription that differs between his left and right eyes where a monovision setting that corresponds to his right eye is enabled for adjustable optics for a display while Sue may have a prescription that is relatively even for both of her eyes where that prescription is enabled for the adjustable optics for the display. As an example, based on input (e.g., credentials, user name, biometrics, etc.), a device may determine an identity of a user and based on such a determination select a prescription that corresponds to that user.

As an example, adjustable optics may include a transparent fluid (e.g., with a refractive index or optionally an adjustable refractive index) that may be selectively delivered to a compartment or compartments to thereby form optics (e.g., a lens or lenses) that can direct light rays emitted by a display. As an example, the compartment or compartments may include an element or elements (e.g., material) that responds to the fluid to change shape with respect to the display. As an example, fluid may be pressurized to adjust optically elements associated with one or more compartments to match a user's prescription. As an example, pressure may be adjusted via an electrical charge to offset focal length for an individual user.

As an example, a system may progress through a range of prescriptions such that a user may input information to indicate a desired prescription. For example, fluid may be subject to increasing pressure to thereby adjust one or more elements and a device may be configured for receipt of an input (e.g., via an input device) to select a state. In such an example, the device may store the state and use the stored state as a prescription. For example, such information may be kept as part of a user profile. As an example, such an approach may accommodate multiple users and adjust automatically when one of the users logs on.

As an example, a system may include a "wizard", for example, consider an application (e.g., executable instructions, etc.) that may be invoked to adjust optical characteristics of adjustable optics to a user. As an example, a wizard may be invoked manually and/or automatically. As an example, where a camera detects a user squinting, a wizard may be invoked and, for example, where a camera detects a user wearing glasses (e.g., or contact lenses), the wizard may be maintained in a suspension state. As an example, a system may include sensing a distance to a user (e.g., an object) and modifying one or more optical properties of adjustable optics to take the distance from the user to the screen into consideration for purposes of adjusting the adjustable optics.

FIG. 1 shows an example of a display 101 with a blurry image 102, as seen by an observer, and an example of a system 103 with a corrected image 104, as seen by an observer, as corrected by an optical correction module 110. In the example of FIG. 1, the dotted lines indicate that physical components of the display 101 and the system 103 may be blurry as well.

FIG. 2 shows examples of some lens types 210 and an example of a system 220 that includes a display 230 and adjustable optics 250. As shown, lens types 210 may include biconvex, plano-convex, convex-concave, meniscus, plano-concave and biconcave. In the example of FIG. 2, the display 230 of the system 220 may include one or more light emitting components, for example, such as one or more backlighting components. As an example, a display may be configured for front lighting, for example, where reflected light allows an observer to discern information rendered to the display. As an example, a display with backlighting, frontlighting, sidelighting, etc. may include adjustable optics. As an example, a display may include liquid crystals, light emitting diodes, etc. As an example, a display may include one or more mirror elements.

As an example, an optical element may be characterized in part by a focus or a focal length. For example, a focal length of an optical system may be a measure of convergence or divergence of light rays. As an example, a focal length may be a distance over which initially collimated rays are brought to a focus. As an example, focal length may be an indication of optical power (e.g., ability to a focus light rays with respect to distance). As an example, an optical element may be characterized in part by a front focal length (FFL) or front focal distance (e.g., distance from a front focal point to the vertex of a first optical surface) and/or a back focal length (BFL) or back focal distance (e.g., distance from the vertex of a last optical surface to a rear focal point). As an example, adjustable optics may provide for alteration of a focus (e.g., or foci).

As an example, a computing device such as a notebook computing device, a tablet computing device, etc. may include an arrangement of components. As an example, a device may optionally include an electromagnetic digitizer panel and a flat panel display (e.g., LCD, etc.) with associated driver circuitry. As an example, a device may include adjustable optics and optionally an electromagnetic digitizer panel. In such an example, a stylus may be provided where the device may receive input via interactions with the stylus. As an example, adjustable optics, where engaged, may allow for receipt of input via interactions between a stylus and an electromagnetic digitizer panel. As an example, an electromagnetic digitizer panel may be disposed toward an inward side, for example, rather than an outward side of a system. For example, layers of a system may include digitizer panel, light emitters/rendering components, and adjustable optics.

In the example of FIG. 2, a user or observer 201 includes one or two eyes 203 that can receive light emitted by the system 220 where the light includes light rays that pass through the adjustable optics 250 (e.g., an adjustable optics overlay, etc.). As an example, the adjustable optics 250 may adjust based in part on information 202 associated with the user 201, for example, identity of the user 201, distance to the user 201, whether the user 201 is wearing glasses, whether the user 201 is wearing contact lenses (e.g., via camera analysis for reflections, etc.), whether the user 201 is squinting, etc. As an example, the system 220 may include one or more inputs for receipt of the user information 202. As an example, a system may be configured to receive one or more prescriptions for one or more users and, for example, to store such information in association with the one or more users. As an example, upon logon (e.g., or other detection technique), a system may access user information that includes prescription information and, in turn, adjust adjustable optics based at least in part on the prescription information.

FIG. 3 shows an example of a system 320 in two states 301 and 303. As shown, the system includes a display 330 and adjustable optics 350. The display 330 is shown as including a planar component 332 that defines a chamber 352 with respect to a component 354 of the adjustable optics 350. As shown, the adjustable optics 350 includes an opening 356 that opens to a compartment 357 that may increase in volume due to an increase in fluid pressure for a fluid in the chamber 352. As shown, the compartment 357 is defined in part by a component 358, which may be flexible to respond to an increase in fluid pressure. As shown in the example of FIG. 3, the compartment 357 is adjustable to form a lens shape, for example, to create an optical element that can alter light rays emitted (e.g., or reflected) by the display 330 of the system 320. In the example of FIG. 3, the state 301 may be referred to as a disengaged state, with respect to the adjustable optics 350, and the state 303 may be referred to as an engaged state, with respect to the adjustable optics 350.

FIG. 3 also shows an example of a system 321 where a component such as the component 354 may be deformable, for example, to form a side of an optical element. As an example, the system 321 may include a component that may include properties that may be adjustable via one or more mechanisms. For example, a component may have one or more elasticity parameters (e.g., Young's modulus) that depend on temperature, electrical charge, pH or other ion concentration, etc. For example, a component may be in a rigid state such that an applied stress does not result in appreciable strain and may be adjusted to an elastic state such that an applied stress results in a desired amount of strain. In such an example, a fluid pressure may apply stress such that the component experiences strain that acts to form at least a portion of an optical element (see, e.g., the lens types 210 of FIG. 2).

FIG. 4 shows examples of lenses 450, 470, 480 and 490. As shown, the lenses 450 and 480 are Fresnel lenses which may be adaptations of plano-convex lenses 470 and 490. As an example, a Fresnel lens may act to conserve space and, for example, allow for implementation of a larger range of optical parameters when compared to a plano-convex lens. For example, the volume of the Fresnel lens 450 is less than the volume of the plano-convex lens 470. In such an example, where fluid is pressurized to adjust optics, a Fresnel lens may be formed using less fluid than an equivalent plano-convex lens. As volume of fluid determines mass, a Fresnel lens formed by adjustable optics may weigh less than an equivalent plano-convex lens formed by adjustable optics.

In FIG. 4, the lenses 480 and 490 are substantially rectangular while the lenses 450 and 470 are substantially round. As an example, adjustable optics may be configured to form a round lens, a rectangular lens or a lens of one or more other shapes.

FIG. 4 illustrates various parameters that may be associated with lenses. For example, FIG. 4 shows focal lengths "f" and "F" as well as a distance "d" between an image and a lens. Further, an example of a magnification equation (e.g., M=F/(F−d)) is shown that depends on the distance "d" and the focal length "F". As an example, the distance "d" may correspond to a distance between a rendering portion of a display and a lens formed by adjustable optics (e.g., whether a Fresnel lens, plano-convex lens or other type of lens). As an example, a system may include a mechanism to adjust a distance such as the distance "d". For example, with respect to the example of FIG. 3, a mechanism may provide for adjusting a distance between the planar component 332 and the component 354. Such a mechanism may adjust a distance, for example, according to a prescription, a desired magnification, etc. As an example, such a mechanism may be electro-mechanical (e.g., worm-gear drive, etc.), pressure driven (e.g., hydraulic, pneumatic, etc.), etc.

FIG. 5 shows examples of systems 520 and 521 where each of the systems 520 and 521 includes a display 530 and adjustable optics 550. The display 530 is shown as including a planar component 532 that defines a chamber 552 with respect to a component 554 of the adjustable optics 550. As shown, the adjustable optics 550 includes an opening 556 that opens to a compartment 557 that may increase in volume due to an increase in fluid pressure for a fluid in the chamber 552. As shown, for the system 520, the compartment 557 is defined in part by a component 558 while, for the system 521, the compartment 557 is defined in part by a component 559, both of which may be flexible to respond to an increase in fluid pressure. As shown in the example of FIG. 5, the compartment 557 is adjustable to form a lens shape, for example, to create an optical element that can alter light rays emitted (e.g., or reflected) by the display 530 of the system 520.

As to the component 559, it may be a component that is relatively flat (e.g., planar) with particular elasticity such that upon application of pressure to one side of the component 559 it forms a Fresnel lens surface (e.g., a Fresnel lens element) that includes a center with a Fresnel zone. In such an example, where pressure is not applied, the component 559 may have substantially constant optical properties, for example, where differences in elasticity do not alter optical properties. As an example, the component 559 may be formed of a polymeric material. As an example, the component 559 may include portions with stiffnesses that differ from other portions. For example, over a Fresnel zone, the component 559 may include rings with high stiffness and rings with low stiffness such that upon application of pressure the low stiffness rings provide for adjusting the high stiffness rings in a manner to form a Fresnel zone of a Fresnel lens. As an example, the component 559 may be made of a single type of material or optionally of different types of materials. For example, portions shown in the example of FIG. 5 that are approximately perpendicular (e.g., normal) to the surface of the component 554 may be formed of an expandable material that expands in a manner to position portions that form lens elements of a Fresnel lens.

FIG. 6 shows an example of unmagnified text and an example of magnified text with respect to a system 620 that includes an optical correction module 610. As shown, in a state 601, the text displayed by the system 620 appears at a first size while, in a state 603, the text displayed by the system 620 appears enlarged (e.g., magnified) to a second size. In such an example, the optical correction module 610 may cause the system 620 to transition from the state 601 to the state 603 (e.g., and vice versa).

FIG. 7 shows an example of unmagnified text and an example of a portion of the text magnified with respect to a system 720 that includes an optical correction module 710. As shown, in a state 701, the text displayed by the system 720 appears at a first size while, in a state 703, a portion of the text 750 displayed by the system 720 appears enlarged (e.g., magnified) to a second size. In such an example, the optical correction module 710 may cause the system 720 to transition from the state 701 to the state 703 (e.g., and vice versa).

As an example, the system 720 may include openings for fluid where fluid may be selectively directed to one or more of the openings (e.g., via fluid channels, etc.). FIG. 7 shows an approximate illustration of openings where black-filled openings represent openings that may have pressures that exceed pressures of other openings, for example, to form one or more optical elements for a portion of the displayed text. As an example, a system may include a microfluidic network that may include fluid channels that may be selectable for pressurization, for example, to form one or more optical elements (e.g., one or more lenses, a portion of a lens, etc.).

As an example, the optical correction module 710 may operate to enlarge text in a serial manner, for example, as for reading. For example, a user may set a speed at which a text window (e.g., a window for a certain number of words) progresses with respect to text. For example, the optical correction module 710 may cause a window to progress at about 5 words per second. In such an example, adjustable optics may respond by selectively engaging an optics adjustment mechanism to create a moving lens or moving lenses with respect to a display. For example, consider the lens 480 or the lens 490 of FIG. 4 as being implemented by adjustable optics for purposes of magnifying text. In such an example, at the end of a block of text, two lenses may optionally be created, for example, one for one row and one for an adjacent row. Such an approach may help enhance a user's viewing experience (e.g., for reading text).

As an example, a device may include an input mechanism to adjust a speed of a moving lens. For example, a scroll wheel of a mouse may be adjustable by a user to increase, decrease, etc. speed of a moving lens. As an example, an input mechanism may provide for stopping a lens, increasing magnification of a lens, decreasing magnification of a lens, enlarging a lens (e.g., to cover more words), diminishing the size of a lens (e.g., to cover fewer words), add lenses, subtract lenses, etc. Such input may be received by an optical correction module that is operatively coupled to adjustable optics, for example, such as adjustable optics of a system that includes a display.

Figure 8:
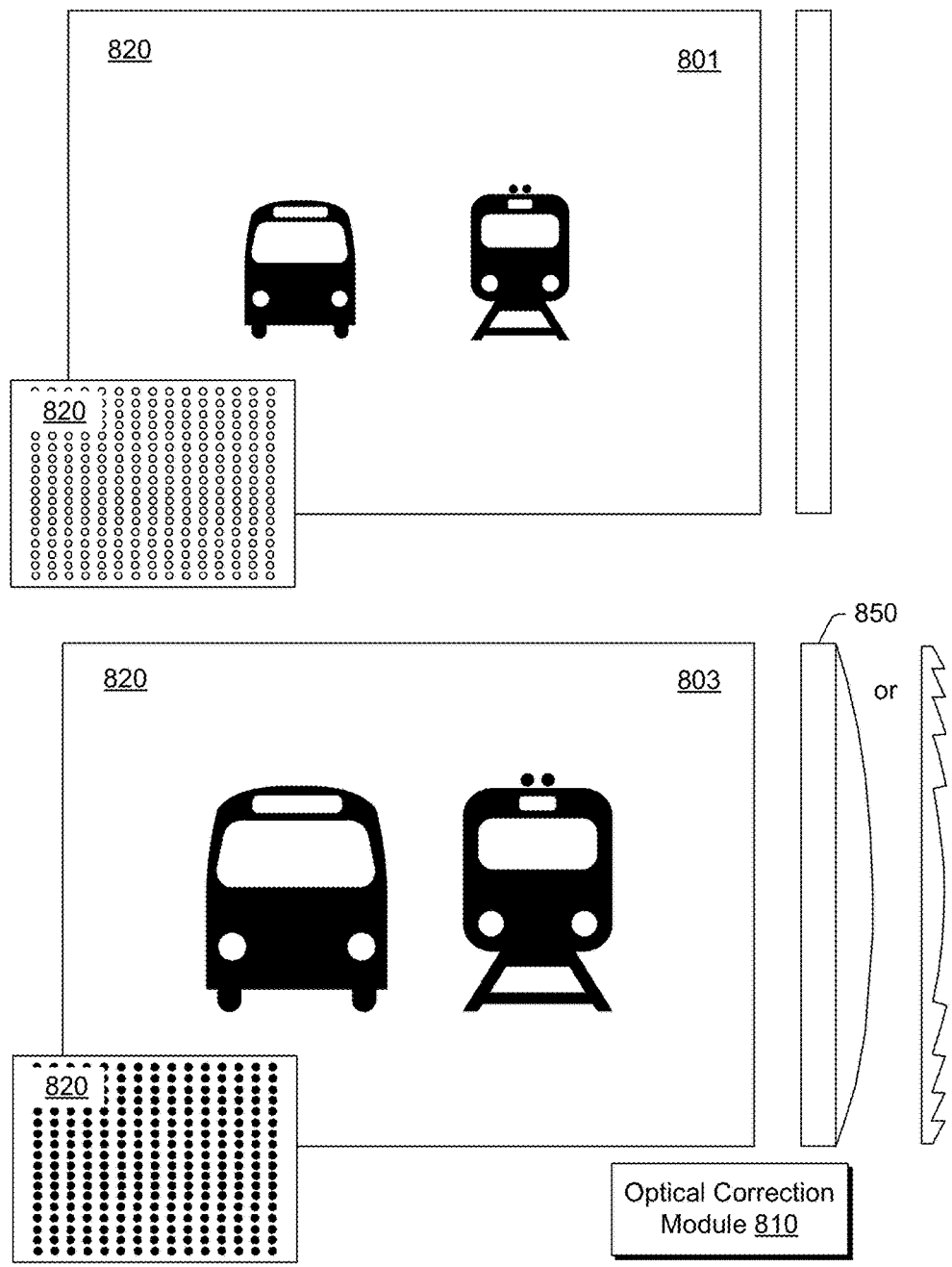
FIG. 8 is a diagram of an example of unmagnified images and an example of magnified images.

FIG. 8 shows an example of unmagnified information and an example of magnified information with respect to a system 820 that includes an optical correction module 810. As shown, in a state 801, the information displayed by the system 820 appears at a first size while, in a state 803, the information displayed by the system 820 appears enlarged (e.g., magnified) to a second size. In such an example, the optical correction module 810 may cause the system 820 to transition from the state 801 to the state 803 (e.g., and vice versa). As an example, the system 820 may include adjustable optics 850 that may be controllable by the optical correction module 810 to form a lens or lenses. For example, consider a plano-convex lens or a Fresnel lens formed by the adjustable optics 850 to enlarge the information displayed by the system 820.

As an example, the system 820 may include openings for fluid where fluid may be selectively directed to one or more of the openings. FIG. 8 shows approximate illustrations of openings where black-filled openings in the state 803 represent openings that may have been pressurized with via a fluidic mechanism, for example, to form one or more optical elements.

Figure 9:
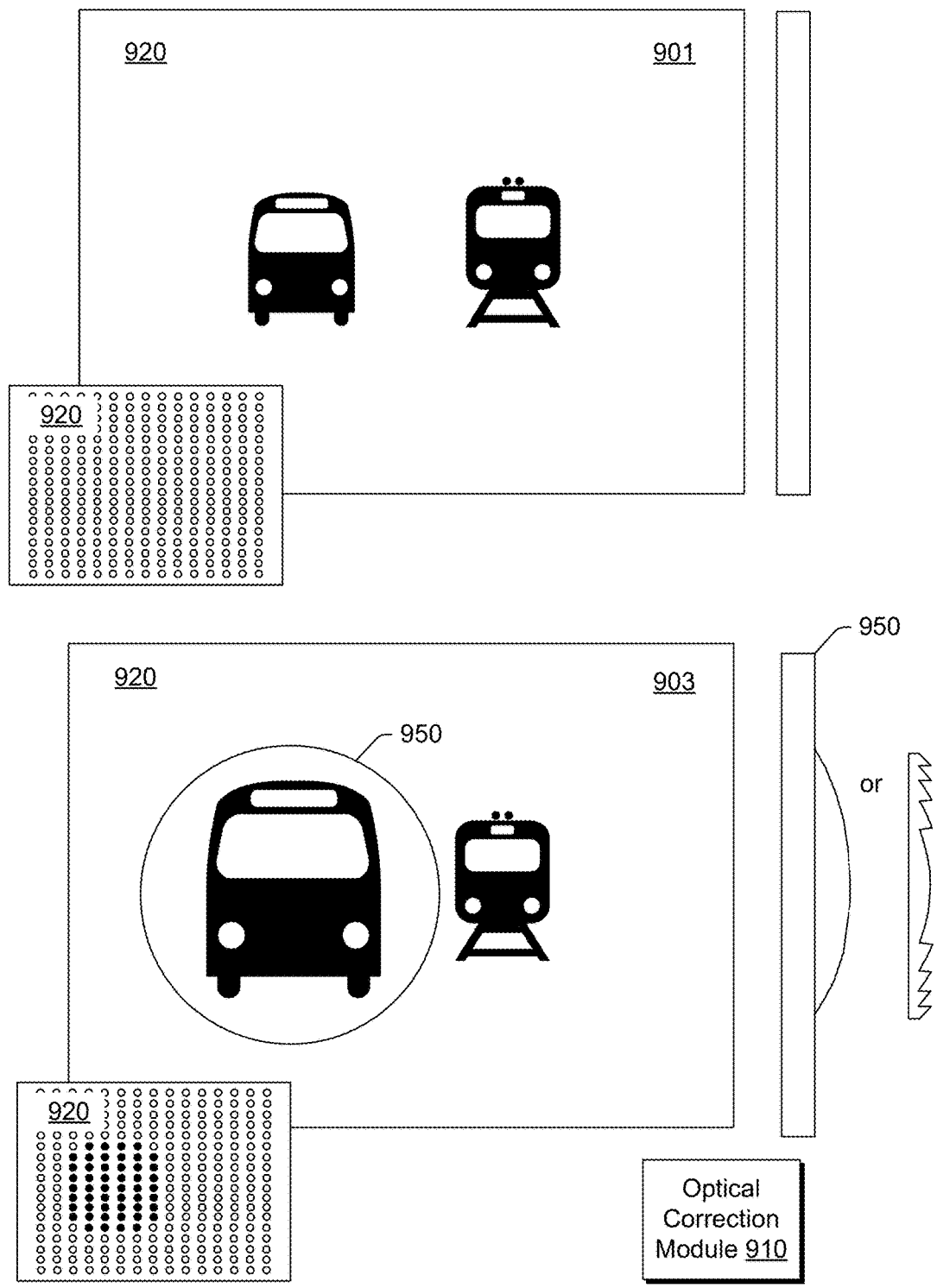
FIG. 9 is a diagram of an example of unmagnified images and an example of one of the images as magnified.

FIG. 9 shows an example of unmagnified information and an example of a portion of the information magnified with respect to a system 920 that includes an optical correction module 910. As shown, in a state 901, the information displayed by the system 920 appears at a first size while, in a state 903, a portion of the information displayed by the system 920 appears enlarged (e.g., magnified) to a second size. In such an example, the optical correction module 910 may cause the system 920 to transition from the state 901 to the state 903 (e.g., and vice versa). As an example, the system 920 may include adjustable optics 950 that may be controllable by the optical correction module 910 to form a lens or lenses. For example, consider a plano-convex lens or a Fresnel lens formed by the adjustable optics 950 to enlarge a portion of the information displayed by the system 920.

As an example, the system 920 may include openings for fluid where fluid may be selectively directed to one or more of the openings. FIG. 9 shows approximate illustrations of openings where black-filled openings in the state 903 represent openings that may have been pressurized with via a fluidic mechanism, for example, to form one or more optical elements.

As an example, a device may include an input mechanism to adjust at least the position of a lens or lenses. As an example, a scroll wheel of a mouse may be adjustable by a user to provide for positioning a lens, increasing magnification of a lens, decreasing magnification of a lens, enlarging a lens (e.g., to cover more words), diminishing the size of a lens (e.g., to cover fewer words), add lenses, subtract lenses, etc. Such input may be received by an optical correction module that is operatively coupled to adjustable optics, for example, such as adjustable optics of a system that includes a display. As an example, by inputting a signal to increase magnification of a lens, an optical correction module may call for increasing fluid pressure to a region of adjustable optics to form an optical element with increased magnification. As an example, a scroll wheel may provide for increasing and decreasing magnification of one or more lenses formed by adjustable optics.

Figure 10:
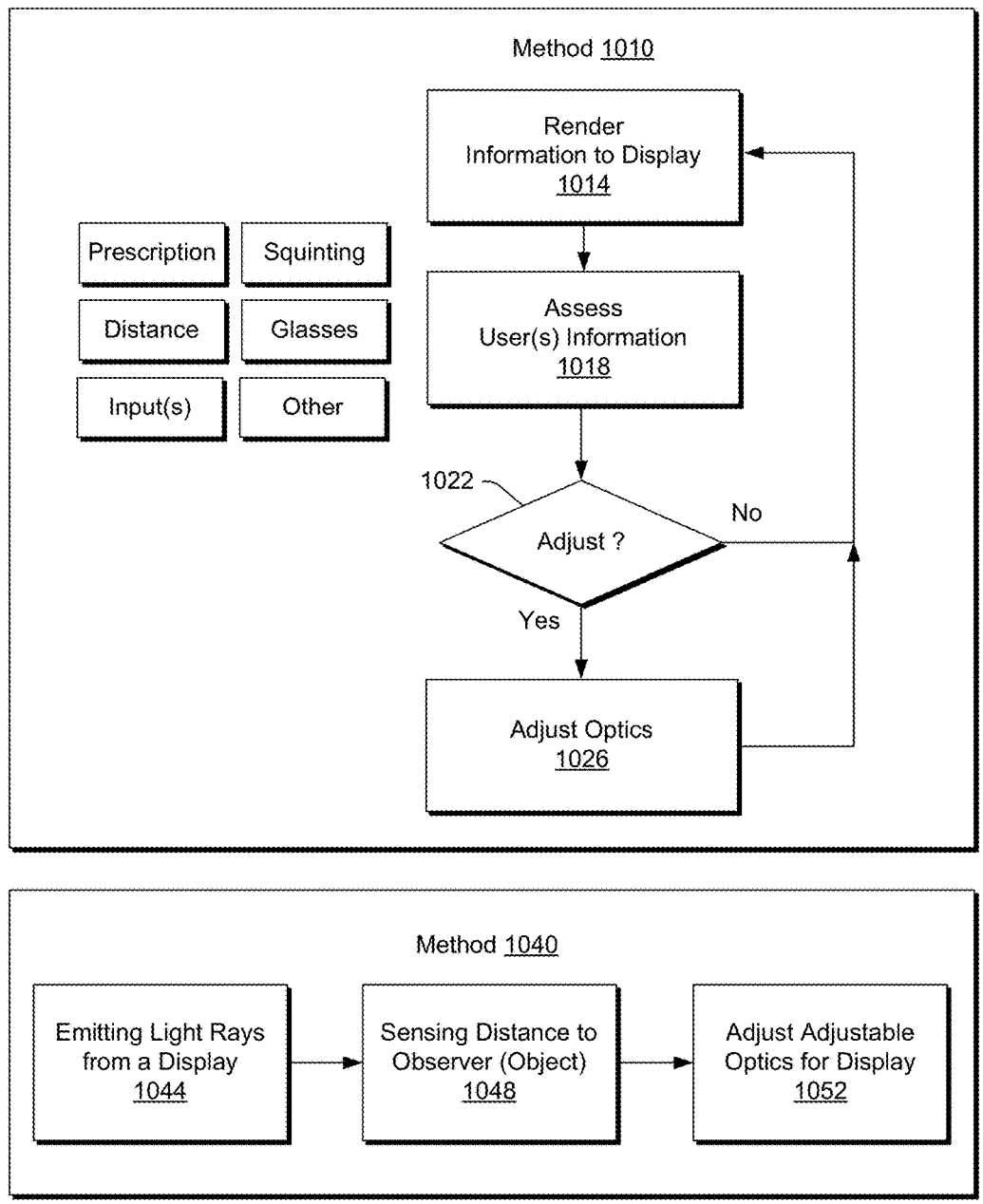
FIG. 10 is a diagram of examples of methods.

FIG. 10 shows examples of methods 1010 and 1040. As shown the method 1010 includes a render block 1014 for rendering information to a display (e.g., including emitting light rays from the display), an assessment block 1018 for assessing information associated with one or more users, a decision block 1022 for deciding whether to adjust adjustable optics based at least in part on the assessed information, and an adjustment block 1026 for adjusting adjustable optics. As shown, the assessment block 1018 may assess information such as a prescription, squinting, distance, glasses (presence or lack thereof), input(s) (e.g., via one or more input mechanisms, etc.) and/or other information.

As shown in FIG. 10, the method 1040 includes an emission block 1044 for emitting light rays from a display, a sense block 1048 for sensing distance to an observer (e.g., an object), and an adjustment block 1052 for adjusting adjustable optics to alter at least some of the emitted light rays from the display.

As an example, a system may include a camera that may be directed outwardly from a display, for example, to acquire information about one or more viewers disposed in a field of view of the display. In such an example, the camera may acquire data and the system may process the data to determine whether a viewer is squinting. For example, data may be processed to determine whether eye size, eye shape, etc. is indicative of squinting. Squinting may be associated with a viewer attempting to increase focus. For example, a decrease in aperture size may increase depth of field akin to adjusting an f-number of a lens (e.g., ratio of a lens' focal length to diameter of an entrance pupil). Depth of field may be defined as a range of distances in object space for which object points are imaged with acceptable sharpness with a fixed position of an image plane.

As an example, a system may include circuitry that acquires information about a viewer, analyzes acquired information about a viewer and that adjusts adjustable optics of the system based on such an analysis. In such an example, squinting and/or lack of squinting may be triggers, for example, for adjusting and halting adjusting of adjustable optics (e.g., according to one or more eye squinting parameters, etc.). For example, detection of squinting by detection circuitry may trigger adjusting and detection of a normal eye size, shape, etc. by detection circuitry may halt adjusting as the adjusting may have arrived at a suitable prescription to accommodate the viewer. In such an example, the system may optionally store viewer information (e.g., identity, etc.), environment information (e.g., distance to viewer, etc.) and one or more settings for adjustable optics. Such an approach may allow the system to more readily adjust to the viewer for a subsequent viewing session.

Figure 11:
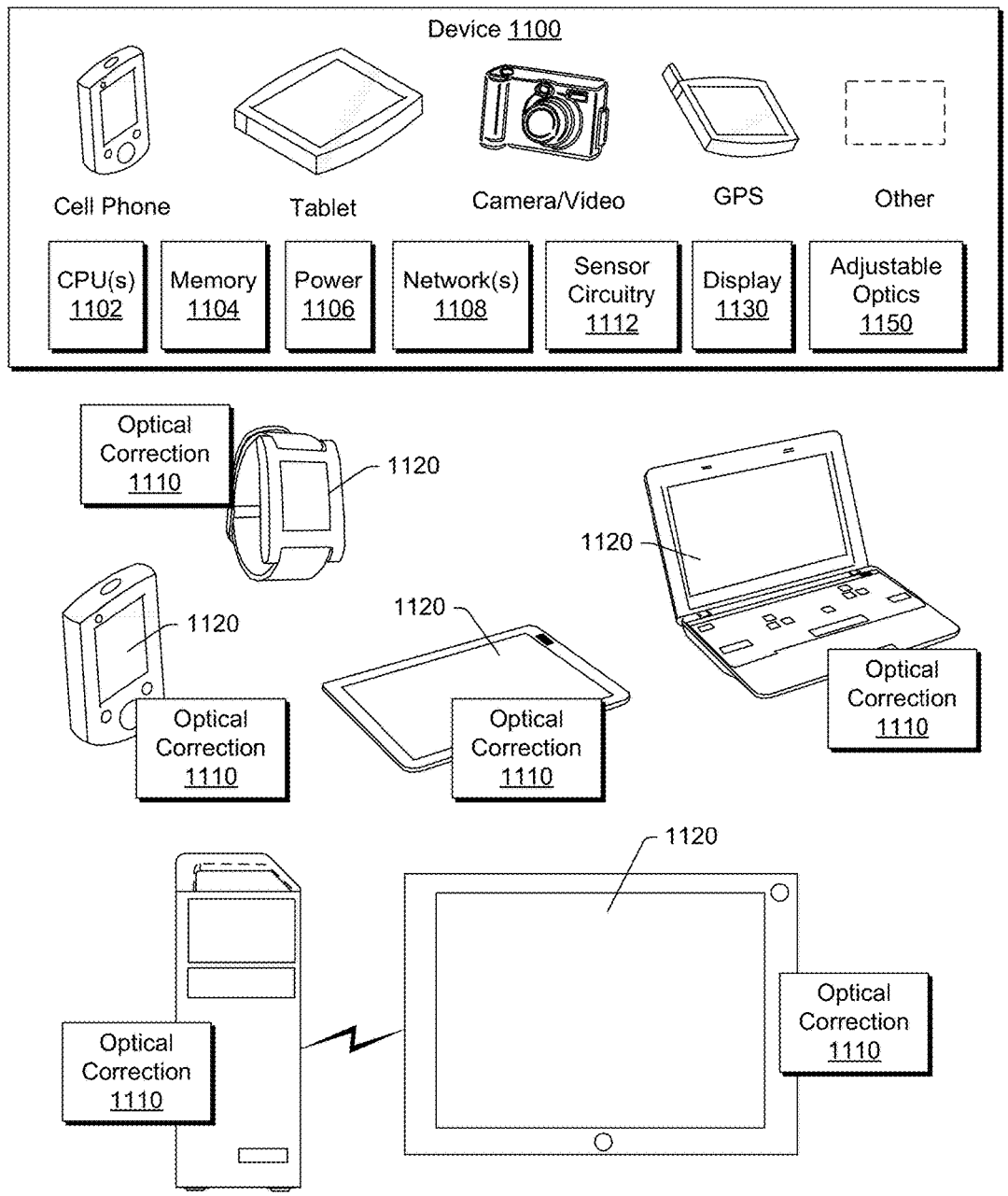
FIG. 11 is a diagram of examples of devices with adjustable optics systems.

FIG. 11 shows an example of a device 1100 that includes a display 1130 and adjustable optics 1150. As shown, the device 1100 may be configured as a watch, a phone, a tablet, a notebook, a desktop system, a camera, a GPS device or other device. As an example, the device 1100 may include one or more processors 1102, memory 1104, a power source 1106, one or more network interfaces 1108, sensor circuitry 1112, a display 1130 (e.g., or displays), and adjustable optics 1150. As shown, a system 1120 may be implemented in a variety of devices where the system 1120 includes a display 1130 and adjustable optics 1150. As an example, a device may include optical correction circuitry 1110 (e.g., an optical correction module). As an example, optical correction circuitry 1110 may be operatively coupled to a processor, may include a processor, etc. As an example, a system may include a panel display and/or a projector that projects light to a viewing panel (e.g., a back-projection projector). In such an example, adjustable optics may be suitably positioned with respect to the display and/or the projector to adjust one or more optical elements through which light rays pass (e.g., to a viewer or viewers disposed in a display's field of view).

As an example, a system can include a display configured to emit light rays; an adjustable-prescription optics overlay; and circuitry to adjust the adjustable-prescription optics overlay to a selected prescription to alter a focus of light rays emitted by at least a portion of the display. In such an example, the adjustable optics overlay may be configured to form a Fresnel lens.

As an example, circuitry to adjust an adjustable optics overlay may include a lens prescription parameter where an adjustment to the adjustable optics overlay by the circuitry depends at least in part on the lens prescription parameter.

As an example, an adjustable optics overlay may include a fluidic network. As an example, a system may include circuitry to that controls fluid pressure in a fluidic network, for example, for formation of one or more lenses (e.g., optical elements). As an example, a fluid may be selected based in part on refractive index. As an example, a water-based liquid may have a refractive index from about 1.33 to about 1.45 and, for example, an organic-based liquid may have a refractive index from about 1.45 to about 1.55. As an example, a high refractive index liquid may have a refractive index greater that about 1.55. As an example, a layer or layers may be made of a material or materials that may be characterized at least in part by a refractive index. As an example, a material or materials may include an adjustable refractive index (e.g., adjustable responsive to temperature, charge, field, etc.).

As an example, an adjustable optics overlay (e.g., adjustable optics) may include ferromagnetic material, for example, consider a ferromagnetic fluid and/or ferromagnetic liquid crystals. In such examples, one or more circuits may provide electromagnetic fields (e.g., or magnetic fields) that can cause the material to orient, shape, etc., for example, to form at least a portion of an optical element.

As an example, a nematic liquid crystal material may be provided as part of an adjustable optics overlay where the nematic liquid crystal material may change refractive index responsive to a change in a field (e.g., electric, magnetic or electromagnetic), for example, to produce a variation of focal length in one or more optical elements. As an example, molecules of nematic liquid crystal material may be rod-shaped, disk-shaped, etc. As an example, for rod-shaped, an average direction of long axes of molecules in a small region may be designated a director of that region. As an example, for disk-shaped, a direction, perpendicular to disks, may define a director. A nematic phase of a nematic liquid crystal material may be characterized in that directors of the material are aligned in a particular direction.

As an example, liquid crystal material may provide for birefringence, for example, splitting of a light ray entering a uniaxial birefringent crystal into two perpendicularly polarized rays, an ordinary ray and an extraordinary ray. In such an example, while the refractive index of the crystal with respect to the ordinary ray tends to be independent of spatial relationship between ray and crystal, the index differs for the extraordinary ray. For example, the refractive index with respect to the extraordinary ray can depend on angle between the incident ray and the optic axis of the crystal. Thus, by varying this angle, for example, by tilting the crystal while keeping the direction of incident light fixed, a variation of refractive index may be achieved with respect to the extraordinary ray in the crystal.

As an example, adjustable optics may employ one or more polarizers, for example, to direct light rays with respect to liquid crystal material, which may be provided as one or more layers of material. In such an example, a field may be adjusted (e.g., via electrodes, an induction coil or coils, etc.) such that directors of the liquid crystal material are tilted toward a particular direction, for example, in a manner related to strength of the field. In turn, the refractive index of the liquid crystal material may change with respect to the incoming polarized ray. As an example, a field (e.g., electric, magnetic or electromagnetic) may be applied at one or more frequencies.

As an example, liquid crystal material may be disposed between layers. In such an example, the layers may be fixed in shape, adjustable in shape or a combination of fixed in shape and adjustable in shape. As an example, a mechanism may adjust shape of at least one layer that may include a surface that borders a liquid crystal material. In such an example, a field may be applied to adjust the refractive index of the liquid crystal material. As an example, liquid crystal material may optionally be pressurized, for example, to form a particular shape and, for example, a field may be applied to adjust the refractive index of the liquid crystal material. In such an example, one or more optical elements may be formed, optionally according to one or more prescriptions. As an example, adjustable optics (e.g., an adjustable optics overlay) may include multiple compartments of liquid crystal material (e.g., bodies of material), for example, distributed over a planar overlay, stacked over a planar overlay or distributed and stacked over a planar overlay.

As an example, an adjustable optics overlay may include liquid crystal material. In such an example, the adjustable optics overlay may include compartments that include liquid crystal material. As an example, such compartments may be adjustable in shape, size, etc.

As mentioned, as an example, adjustable optics may include one or more components that are elastic, for example, to form at least a portion of one or more optical elements responsive to pressure. As an example, adjustable optics may include one or more components that have an adjustable Young's modulus, for example, to form at least a portion of one or more optical elements (e.g., responsive to applied stress).

As an example, an adjustable optics overlay may include rings, for example, where the rings are adjustable to form a Fresnel zone (e.g., optionally in response to fluid pressure or other adjustment mechanism). As an example, a Fresnel lens may be formed at least in part using liquid crystal material where the liquid crystal material may be adjustable with respect to refractive index. As an example, a layer may be adjustable to form a ring or rings of a Fresnel zone (e.g., via a pressure mechanism) and, for example, a field may be applied to adjust refractive index of a material, which may be disposed adjacent to the layer. In such an example, an adjustable optics overlay may selectively form a Fresnel lens (e.g., over at least a portion of a display system) and adjust one or more characteristics of the lens (e.g., refractive index, etc.).

As an example, an adjustable optics overlay may include features configured to form circular optical structures and configured to form annular optical structures. In such an example, a structure (e.g., a lens) may be formed with a circular optical structure surrounded by a plurality of annular optical structures.

As an example, a system may include sensing circuitry to sense distance between a display and an object (e.g., an observer, a user, etc.). In such an example, circuitry to adjust adjustable optics (e.g., an adjustable optics overlay) may include a distance parameter where an adjustment to the adjustable optics by the circuitry depends at least in part on the distance parameter.

As an example, a system may include detection circuitry to detect eye squinting (e.g., including lack of squinting, etc.). In such an example, circuitry to adjust an adjustable optics overlay may include an eye squinting parameter where an adjustment to the adjustable optics overlay by the circuitry depends at least in part on the eye squinting parameter.

As an example, a system may include sensing circuitry to sense eye movement, for example, to control movement of a lens or lenses. In such an example, circuitry to adjust an adjustable optics overlay may include an eye movement parameter where an adjustment to the adjustable optics overlay by the circuitry depends at least in part on the eye movement parameter.

As an example, a system can include a processor; memory operatively coupled to the processor; a display operatively coupled to the processor where the display is configured to emit light rays and where the display includes adjustable optics; and circuitry to adjust the adjustable optics to alter a focus of light rays emitted by at least a portion of the display. In such an example, the system may include a user parameter where the circuitry to adjust is configured to adjust the adjustable optics based at least in part on the user parameter.

As an example, a method can include emitting light rays from a display; sensing a distance from the display to an object; and based at least in part on the distance, adjusting adjustable optics associated with the display to alter a focus of at least a portion of the light rays. In such an example, adjusting the adjustable optics may include forming a Fresnel lens (e.g., via one or more mechanisms).

As described herein, various acts, steps, etc., may be implemented as instructions stored in one or more computer-readable storage media. For example, one or more computer-readable storage media can include computer-executable (e.g., processor-executable) instructions to instruct a device. A computer-readable medium may be a computer-readable medium that is not a carrier wave.

The term "circuit" or "circuitry" is used in the summary, description, and/or claims. As is well known in the art, the term "circuitry" includes all levels of available integration, e.g., from discrete logic circuits to the highest level of circuit integration such as VLSI, and includes programmable logic components programmed to perform the functions of an embodiment as well as general-purpose or special-purpose processors programmed with instructions to perform those functions. Such circuitry may optionally rely on one or more computer-readable media that includes computer-executable instructions. As described herein, a computer-readable medium may be a storage device (e.g., a memory chip, a memory card, a storage disk, etc.) and referred to as a computer-readable storage medium.

Figure 12:
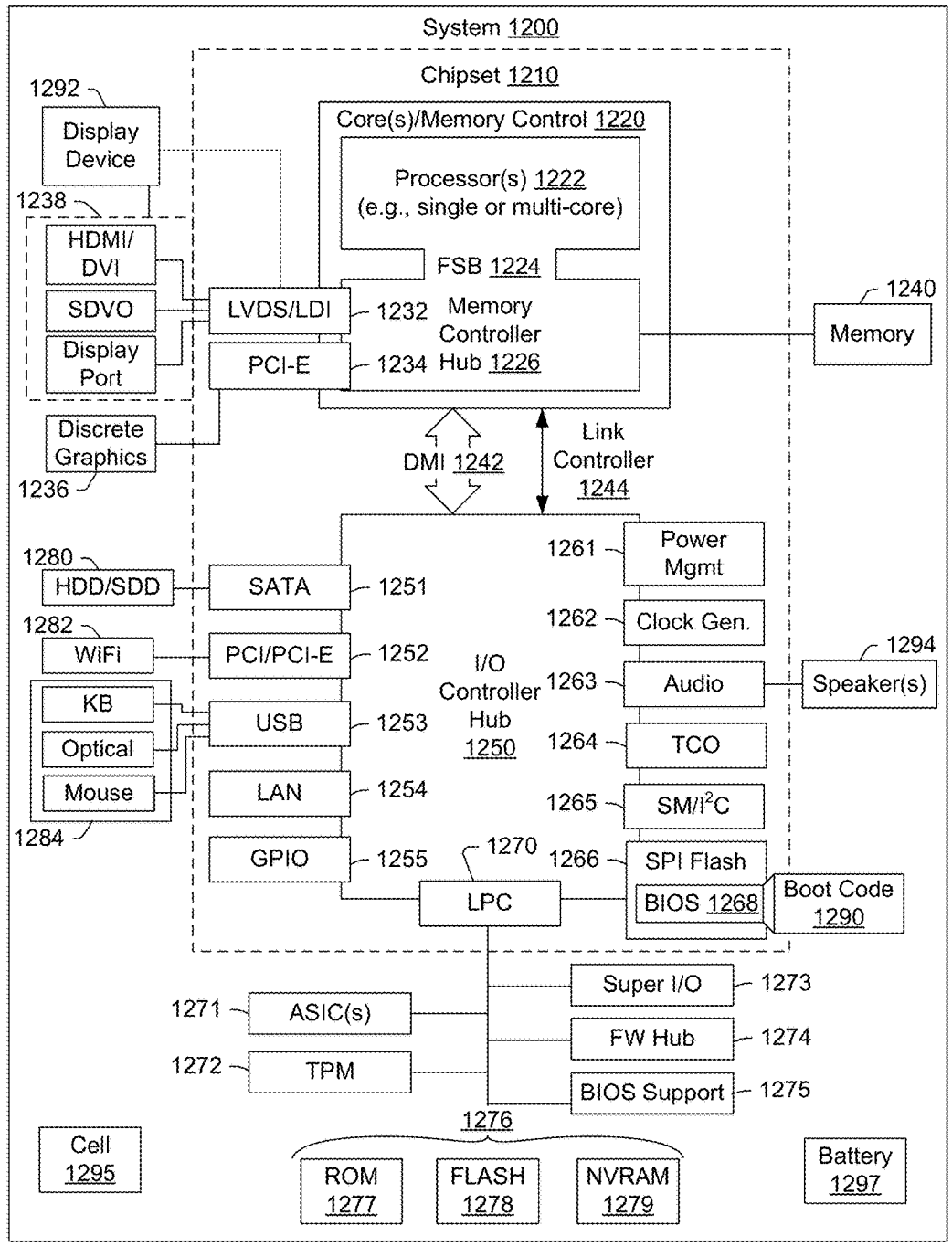
FIG. 12 is a diagram of an example of a system that includes one or more processors.

While various examples of circuits or circuitry have been discussed, FIG. 12 depicts a block diagram of an illustrative computer system 1200. The system 1200 may be a desktop computer system, such as one of the ThinkCentre® or ThinkPad® series of personal computers sold by Lenovo (US) Inc. of Morrisville, N.C., or a workstation computer, such as the ThinkStation®, which are sold by Lenovo (US) Inc. of Morrisville, N.C.; however, as apparent from the description herein, a satellite, a base, a server or other machine may include other features or only some of the features of the system 1200. As an example, a device such as one of the devices of FIG. 11 may include at least some of the features of the system 1200.

As shown in FIG. 12, the system 1200 includes a so-called chipset 1210. A chipset refers to a group of integrated circuits, or chips, that are designed (e.g., configured) to work together. Chipsets are usually marketed as a single product (e.g., consider chipsets marketed under the brands INTEL®, AMD®, etc.).

In the example of FIG. 12, the chipset 1210 has a particular architecture, which may vary to some extent depending on brand or manufacturer. The architecture of the chipset 1210 includes a core and memory control group 1220 and an I/O controller hub 1250 that exchange information (e.g., data, signals, commands, etc.) via, for example, a direct management interface or direct media interface (DMI) 1242 or a link controller 1244. In the example of FIG. 12, the DMI 1242 is a chip-to-chip interface (sometimes referred to as being a link between a "northbridge" and a "southbridge").

The core and memory control group 1220 include one or more processors 1222 (e.g., single core or multi-core) and a memory controller hub 1226 that exchange information via a front side bus (FSB) 1224. As described herein, various components of the core and memory control group 1220 may be integrated onto a single processor die, for example, to make a chip that supplants the conventional "northbridge" style architecture.

The memory controller hub 1226 interfaces with memory 1240. For example, the memory controller hub 1226 may provide support for DDR SDRAM memory (e.g., DDR, DDR2, DDR3, etc.). In general, the memory 1240 is a type of random-access memory (RAM). It is often referred to as "system memory".

The memory controller hub 1226 further includes a low-voltage differential signaling interface (LVDS) 1232. The LVDS 1232 may be a so-called LVDS Display Interface (LDI) for support of a display device 1292 (e.g., a CRT, a flat panel, a projector, etc.). A block 1238 includes some examples of technologies that may be supported via the LVDS interface 1232 (e.g., serial digital video, HDMI/DVI, display port). The memory controller hub 1226 also includes one or more PCI-express interfaces (PCI-E) 1234, for example, for support of discrete graphics 1236. Discrete graphics using a PCI-E interface has become an alternative approach to an accelerated graphics port (AGP). For example, the memory controller hub 1226 may include a 16-lane (×16) PCI-E port for an external PCI-E-based graphics card. A system may include AGP or PCI-E for support of graphics. As described herein, a display may be a sensor display (e.g., configured for receipt of input using a stylus, a finger, etc.). As described herein, a sensor display may rely on resistive sensing, optical sensing, or other type of sensing.

The I/O hub controller 1250 includes a variety of interfaces. The example of FIG. 12 includes a SATA interface 1251, one or more PCI-E interfaces 1252 (optionally one or more legacy PCI interfaces), one or more USB interfaces 1253, a LAN interface 1254 (more generally a network interface), a general purpose I/O interface (GPIO) 1255, a low-pin count (LPC) interface 1270, a power management interface 1261, a clock generator interface 1262, an audio interface 1263 (e.g., for speakers 1294), a total cost of operation (TCO) interface 1264, a system management bus interface (e.g., a multi-master serial computer bus interface) 1265, and a serial peripheral flash memory/controller interface (SPI Flash) 1266, which, in the example of FIG. 12, includes BIOS 1268 and boot code 1290. With respect to network connections, the I/O hub controller 1250 may include integrated gigabit Ethernet controller lines multiplexed with a PCI-E interface port. Other network features may operate independent of a PCI-E interface.

The interfaces of the I/O hub controller 1250 provide for communication with various devices, networks, etc. For example, the SATA interface 1251 provides for reading, writing or reading and writing information on one or more drives 1280 such as HDDs, SDDs or a combination thereof. The I/O hub controller 1250 may also include an advanced host controller interface (AHCI) to support one or more drives 1280. The PCI-E interface 1252 allows for wireless connections 1282 to devices, networks, etc. The USB interface 1253 provides for input devices 1284 such as keyboards (KB), one or more optical sensors, mice and various other devices (e.g., microphones, cameras, phones, storage, media players, etc.). On or more other types of sensors may optionally rely on the USB interface 1253 or another interface (e.g., I$^2$C, etc.). As to microphones, the system 1200 of FIG. 12 may include hardware (e.g., audio card) appropriately configured for receipt of sound (e.g., user voice, ambient sound, etc.).

In the example of FIG. 12, the LPC interface 1270 provides for use of one or more ASICs 1271, a trusted platform module (TPM) 1272, a super I/O 1273, a firmware hub 1274, BIOS support 1275 as well as various types of memory 1276 such as ROM 1277, Flash 1278, and non-volatile RAM (NVRAM) 1279. With respect to the TPM 1272, this module may be in the form of a chip that can be used to authenticate software and hardware devices. For example, a TPM may be capable of performing platform authentication and may be used to verify that a system seeking access is the expected system.

The system 1200, upon power on, may be configured to execute boot code 1290 for the BIOS 1268, as stored within the SPI Flash 1266, and thereafter processes data under the control of one or more operating systems and application software (e.g., stored in system memory 1240). An operating system may be stored in any of a variety of locations and accessed, for example, according to instructions of the BIOS 1268. Again, as described herein, a satellite, a base, a server or other machine may include fewer or more features than shown in the system 1200 of FIG. 12. Further, the system 1200 of FIG. 12 is shown as optionally include cell phone circuitry 1295, which may include GSM, CDMA, etc., types of circuitry configured for coordinated operation with one or more of the other features of the system 1200. Also shown in FIG. 12 is battery circuitry 1297, which may provide one or more battery, power, etc., associated features (e.g., optionally to instruct one or more other components of the system 1200). As an example, a SMBus may be operable via a LPC (see, e.g., the LPC interface 1270), via an I$^2$C interface (see, e.g., the SM/I$^2$C interface 1265), etc.

CONCLUSION

Although examples of methods, devices, systems, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, etc.

What is claimed is:

1. A system comprising:
a display that emits light rays;
an adjustable-prescription optics overlay; and
circuitry that adjusts the adjustable-prescription optics overlay to a selected prescription to alter a focus of light rays emitted by at least a portion of the display wherein an adjustment to the adjustable-prescription optics overlay by the circuitry depends at least in part on a lens prescription parameter.

2. The system of claim 1 wherein the adjustable-prescription optics overlay is configured to form a Fresnel lens.

3. The system of claim 1 wherein the adjustable-prescription optics overlay comprises a fluidic network.

4. The system of claim 3 wherein the circuitry to adjust is configured to control fluid pressure in the fluidic network.

5. The system of claim 1 wherein the adjustable-prescription optics overlay comprises liquid crystal material.

6. The system of claim 5 comprising compartments that comprise at least a portion of the liquid crystal material.

7. The system of claim 1 wherein the adjustable-prescription optics overlay comprises a ferromagnetic fluid.

8. The system of claim 1 wherein the adjustable-prescription optics overlay comprises rings.

9. The system of claim 8 wherein the rings are adjustable to form a Fresnel zone.

10. The system of claim 1 wherein the adjustable-prescription optics overlay comprises features configured to form circular optical structures and configured to form annular optical structures.

11. The system of claim 10 wherein the adjustable-prescription optics overlay comprises features configured to form a circular optical structure surrounded by a plurality of annular optical structures.

12. The system of claim 1 comprising sensing circuitry to sense distance between the display and an object.

13. The system of claim 12 wherein the circuitry to adjust comprises a distance parameter wherein an adjustment to the adjustable-prescription optics overlay by the circuitry depends at least in part on the distance parameter.

14. The system of claim 1 comprising detection circuitry to detect eye squinting.

15. The system of claim 14 wherein the circuitry to adjust comprises an eye squinting parameter wherein an adjustment to the adjustable-prescription optics overlay by the circuitry depends at least in part on the eye squinting parameter.

16. A system comprising:
a processor;
memory operatively coupled to the processor;
a display operatively coupled to the processor wherein the display emits light rays and wherein the display comprises adjustable optics; and
circuitry that adjusts the adjustable optics based at least in part on a user parameter to alter a focus of light rays emitted by at least a portion of the display.

* * * * *